(12) United States Patent
Zhong et al.

(10) Patent No.: US 6,261,761 B1
(45) Date of Patent: Jul. 17, 2001

(54) NF1 PROTEIN AND ITS ROLE IN ACTIVATION OF ADENYLYL CYCLASE BY PACAP38-LIKE NEUROPEPTIDES

(75) Inventors: Yi Zhong; Hui-Fu Guo, both of Huntington, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 09/542,331

(22) Filed: Apr. 4, 2000

Related U.S. Application Data

(63) Continuation of application No. 09/046,745, filed on Mar. 24, 1998, now abandoned.
(60) Provisional application No. 60/041,469, filed on Mar. 24, 1997.

(51) Int. Cl.[7] ........................................... C12Q 1/00
(52) U.S. Cl. ................................................... 435/4
(58) Field of Search ....................................... 435/4

(56) References Cited

U.S. PATENT DOCUMENTS 5,859,195   1/1999   Collins et al. .................. 530/350

FOREIGN PATENT DOCUMENTS

WO 92/00387   1/1992   (WO).

OTHER PUBLICATIONS

Silva, A.J., et al. "A mouse model for the learning and memory deficits associated with neurofibromatosis type 1." *Nature Genetics.* 15:281–284 (1997).

Primary Examiner—Robert A. Schwartzman
Assistant Examiner—Katharine F Davis
(74) Attorney, Agent, or Firm—Hamilton, Brook, Smith & Reynolds, P.C.

(57) ABSTRACT

Neurofibromatosis type 1 (NF1) protein loss is associated with a variety of disorders. This protein is involved in the metabolic pathway to produce cyclic AMP via G protein-coupled receptors. Loss in the amount or activity of NF1 protein causes loss of cyclic AMP formation and therefore, loss of subsequent protein kinase A activation. Administration of NF1 protein or an inducible gene that encodes NF1 protein to individuals with diseases associated with loss of functional NF1 protein results in a satisfactory treatment of the disease.

3 Claims, 2 Drawing Sheets

SEQUENCE LISTING

```
<160> NUMBER OF SEQ ID NOS: 3

<210> SEQ ID NO 1
<211> LENGTH: 2802
<212> TYPE: PRT
<213> ORGANISM: Drosophila

<400> SEQUENCE: 1

Met Thr Gln Lys Pro Gly Glu Trp Ala Ser Ala Leu Leu Ala Arg Phe
 1               5                  10                  15

Glu Asp Gln Leu Pro Asn Arg Ile Gly Ala Tyr Gly Thr Gln Ala Arg
             20                  25                  30

Met Ser Gln Asp Gln Leu Val Ala Cys Leu Ile His Ile Ser Arg Tyr
         35                  40                  45

Arg Phe Ser Leu Val Ile Ser Gly Leu Thr Lys Met Leu Gln Arg Val
     50                  55                  60

Asn Glu Ala Ala Leu Gln Asn Arg His Glu Pro Glu Arg Cys Tyr Phe
 65                  70                  75                  80

Glu Ser Leu Val Ile Ile Leu Thr Thr Leu Glu Arg Cys Leu Thr Asn
                 85                  90                  95

Gln Thr Lys Asp Thr Ala Arg Phe Glu Glu Ala Met Asn Val Lys Leu
            100                 105                 110

Leu Leu Arg Glu Ile Ser Gln Phe Val Asp Val Gln Ser Asp Ser Asn
        115                 120                 125

Pro Asn Ala Ala Gln Leu Lys Ala Leu Ala Ser Lys Val Leu Phe Ala
    130                 135                 140

Leu Ser Gln Asn His Phe Ser Ala Val Phe Asn Arg Ile Ser Ala Arg
145                 150                 155                 160

Ile Gln Glu Leu Thr Ser Cys Ser Glu Glu Asn Pro Asp Tyr Asn Asp
                165                 170                 175

Ile Glu Leu Ile Gln His Ile Asp Met Asp Met Ile Lys Leu Thr Lys
            180                 185                 190

Leu Leu Gln Glu Thr Ile Thr Lys Phe Arg Ser Lys Arg Ala Pro Pro
        195                 200                 205
```

-continued

```
Leu Ile Leu Leu Tyr Ser Leu Glu Lys Ala Ile Trp Asn Trp Ile Glu
    210                 215                 220
Tyr His Pro Gln Glu Phe Gln Asp Leu Gln Arg Gly Thr Asn Arg Asp
225                 230                 235                 240
Ile Ser Thr Cys Trp Glu Pro Leu Met Asp Phe Val Glu Tyr Phe Lys
                245                 250                 255
Thr Glu Asn Lys Lys Ser Lys Thr Leu Val Trp Pro Leu Gln Met Leu
            260                 265                 270
Leu Leu Ile Leu Asn Pro Ser Cys Leu Glu Ala Val Asn Glu Leu
        275                 280                 285
Gln Gln Ser Glu Lys Glu Lys Glu Lys Asp Lys Glu Lys Val Ala Ser
    290                 295                 300
Lys Ser Ala Gln Ser Thr Ser Arg Asp Lys Asp Phe Ser Ala Lys Gln
305                 310                 315                 320
Phe Ile Glu Ser Ile Lys Arg Gly Leu Gly Gln His Ser Pro Ser Lys
                325                 330                 335
Gln Val Thr Glu Ser Ala Ala Ile Ala Cys Val Lys Leu Cys Lys Ala
            340                 345                 350
Ser Thr Tyr Ile Asn Asn Thr Asp Ser Asn Asn Val Val Phe Lys Leu
        355                 360                 365
Val Gln Phe Phe Ile Asn Asp Leu Lys Ala Leu Leu Phe Asn Pro Ala
    370                 375                 380
Lys Pro Phe Ser Arg Gly Gln Gly Tyr Asn Phe Ala Asp Ile Glu Leu
385                 390                 395                 400
Met Ile Asp Cys Trp Val Ser Cys Phe Arg Ile Asn Pro His Asn Ile
                405                 410                 415
Glu Ala Leu Lys Val Cys Leu Asn Leu Ser Ser Pro Gln Ala Tyr His
            420                 425                 430
Phe Val Ile Val Cys Ser Leu Leu Arg Leu Ala His Ile Tyr Val Asp
        435                 440                 445
Phe Arg Leu Gln Asn Lys Asn Pro Phe Arg Ile Val Asn Gln Pro Arg
    450                 455                 460
Leu Ser Trp Trp Pro Gln Thr Asp Val Val His Tyr Arg Ser Ala Glu
465                 470                 475                 480
Leu Arg Ala Leu Phe Thr Asp Thr Leu Asn Lys Ala Thr Gln Gly Tyr
                485                 490                 495
Ile Ala His Thr Pro Leu Arg Tyr Ile Thr Ser Leu Thr Leu Lys Ser
            500                 505                 510
Lys Asp Thr Gln Lys Gly Leu Thr Arg Ala Glu Glu Gly Pro Ala His
        515                 520                 525
Lys Met Leu Leu Leu Leu Val Arg Leu Ile His Ala Asp Pro Thr
    530                 535                 540
Leu Leu Leu Asn Thr Gln Gly Lys Val Ala His Glu Val Gln Ser Ser
545                 550                 555                 560
Thr Leu Glu Leu Ile Asn Gly Leu Val Ser Leu Val His Gln Thr Thr
                565                 570                 575
Met Pro Asp Val Ala Gln Glu Ala Met Glu Ala Leu Leu Ala Leu His
            580                 585                 590
Ala Pro Glu Lys Ile Glu Val Trp Asn Pro Glu Ala Pro Ile Asn Thr
        595                 600                 605
Phe Trp Asp Val Ser Ser Gln Val Leu Phe Ser Ile Ser Gln Lys Leu
    610                 615                 620
```

-continued

```
Ile Gln His Gln Ile Ala Asn Tyr Thr Asp Val Leu Lys Trp Leu Arg
625                 630                 635                 640

Glu Ile Leu Ile Cys Arg Asn Thr Phe Leu Gln Arg His Lys Asp Tyr
                645                 650                 655

Ala His Val Gly Ser Gln Ile Ala Ile Cys Lys Gln Ala His Ile Lys
                660                 665                 670

Met Glu Val Val Phe Phe Met Tyr Leu Trp Ser Val Asp Leu Asp Ala
                675                 680                 685

Val Leu Thr Ser Leu Ser Cys Phe Gly Leu Leu Cys Glu Glu Ala Glu
        690                 695                 700

Ile Cys Cys Ser Ser Asp Glu Leu Thr Val Gly Phe Ile Met Pro Asn
705                 710                 715                 720

Tyr His Ile Tyr Gln Glu Leu Ala Gln Leu Ser Thr Ser Ala Thr Asp
                725                 730                 735

Ser Arg Ile Cys Phe Phe Asp Asn Thr His Gly Asn Val Leu Ser Arg
                740                 745                 750

Leu Thr Leu Gln Lys Arg Ile Met Thr Leu Leu Arg Lys Ile Glu His
        755                 760                 765

Cys Val His Gly Val Gln Pro Ala Trp Glu Glu Thr Phe Arg Asn Trp
770                 775                 780

Glu Val Ser Ser Lys Val Leu Gln Thr Tyr Pro Lys Cys Lys Gly Glu
785                 790                 795                 800

Asp Gly Gln Ala Glu Val Phe His Arg Gly Met Gly Lys Arg Arg Ala
                805                 810                 815

Ser His Gln Ser Ser Glu His Asp Leu Glu Glu Gln Ile Asn Glu Trp
                820                 825                 830

Ala Asn Met Thr Trp Phe Leu Leu Ala Leu Gly Gly Val Cys Leu His
        835                 840                 845

Lys Arg Ser Ser Arg Gln Met Leu Leu Gln Ser Gln Asn Asn
850                 855                 860

Ala Ser Leu Gly Ser Leu Ala Gln Asn Ser Leu Tyr Ser Ser Ser Thr
865                 870                 875                 880

Ser Ser Gly His Gly Ser Leu His Pro Ser Thr Val Ser Leu Ser Thr
                885                 890                 895

Leu Pro Pro Ala Pro Gln Asp Val Ser Tyr Cys Pro Val Thr Gln
                900                 905                 910

Phe Val Gly Gln Leu Leu Arg Leu Leu Val Cys Ser Asn Glu Lys Ile
                915                 920                 925

Gly Leu Asn Ile Gln Lys Asn Val Lys Glu Leu Val Gly Glu Glu Met
        930                 935                 940

Ser Thr Gln Leu Tyr Pro Ile Leu Phe Asp Gln Val Arg Ala Ile Val
945                 950                 955                 960

Glu Lys Phe Phe Asp Gln Gln Gly Gln Val Asn Val Asn Val Thr Asp
                965                 970                 975

Ile Asn Thr Gln Phe Ile Glu His Thr Ile Tyr Ile Met Lys Ser Ile
                980                 985                 990

Leu Asp Pro Lys Ala Asn Lys Asp Pro Asn Asn Asp Gln Pro Ser Pro
        995                 1000                1005

Ser Glu His Leu Gly Val Thr Ser Ile Glu Gly Met Met Leu Gly Ile
        1010                1015                1020

Val Arg Tyr Val Arg His Leu Asp Met Thr Val Tyr Ala Ile Arg Ile
1025                1030                1035                1040

Lys Thr Lys Leu Cys Gln Leu Val Glu Val Met Met Lys Arg Arg Asp
```

```
                   1045                1050                1055
Asp Leu Ala Phe Arg Gln Glu Met Lys Phe Arg Asn Lys Leu Val Glu
                1060                1065                1070
Tyr Leu Thr Asp Trp Val Met Gly Thr Ser His Gln Ile Ala Pro Pro
            1075                1080                1085
Ser Ser Ala Asp Ala Ala Ile Leu Thr Asn Thr Ser Leu Ile Phe Arg
        1090                1095                1100
Asp Leu Asp Gln Ala Cys Met Glu Ala Val Ala Ala Leu Leu Arg Gly
1105                1110                1115                1120
Leu Pro Leu Gln Pro Glu Glu Ser Asp Arg Gly Asp Leu Met Asp Ala
                1125                1130                1135
Lys Ser Ala Leu Phe Leu Lys Tyr Phe Thr Leu Phe Met Asn Leu Leu
            1140                1145                1150
Asn Asp Cys Ile Asp Ser Ser Glu Ala Glu Lys Glu Met Asn Asn Thr
        1155                1160                1165
Pro Leu Leu Pro Pro Arg Pro Pro Met Ala Ala Gly Lys Leu Thr Ala
    1170                1175                1180
Leu Arg Asn Ala Thr Ile Leu Ala Met Ser Asn Leu Leu Gly Ala Asn
1185                1190                1195                1200
Ile Asp Ser Gly Leu Met His Ser Ile Asp Leu Gly Tyr Asn Pro Asp
                1205                1210                1215
Leu Gln Thr Arg Ala Ala Phe Met Glu Val Leu Thr Gln Ile Leu Gln
            1220                1225                1230
Gln Gly Thr Glu Phe Asp Thr Leu Ala Glu Thr Val Leu Ala Asp Arg
        1235                1240                1245
Phe Glu Gln Leu Val Gln Leu Val Thr Met Ile Ser Asp Lys Gly Glu
    1250                1255                1260
Leu Pro Ile Ala Met Ala Leu Ala Asn Val Val Thr Thr Ser Gln Met
1265                1270                1275                1280
Asp Glu Leu Ala Arg Val Leu Val Thr Leu Phe Asp Ala Lys His Leu
                1285                1290                1295
Leu Ser Pro Leu Leu Trp Asn Met Phe Tyr Arg Glu Val Glu Val Ser
            1300                1305                1310
Asp Cys Met Gln Thr Leu Phe Arg Gly Asn Ser Leu Gly Ser Lys Ile
        1315                1320                1325
Met Ala Phe Cys Phe Lys Ile Tyr Gly Ala Ser Tyr Leu Gln Met Leu
    1330                1335                1340
Leu Glu Pro Leu Ile Arg Pro Leu Leu Asp Glu Glu Glu Thr Cys
1345                1350                1355                1360
Phe Glu Val Asp Pro Ala Arg Leu Asp Pro Thr Glu Asp Ile Glu Gln
                1365                1370                1375
His Arg Asn Asn Leu Ile Ala Leu Thr Gln Lys Val Phe Asp Ala Ile
            1380                1385                1390
Ile Asn Ser Ser Asp Arg Phe Pro Pro Gln Leu Arg Ser Met Cys His
        1395                1400                1405
Cys Leu Tyr Gln Val Leu Ser Lys Arg Phe Pro Asn Leu Leu Gln Asn
    1410                1415                1420
Asn Ile Gly Ala Val Gly Thr Val Ile Phe Leu Arg Phe Ile Asn Pro
1425                1430                1435                1440
Ala Ile Val Ser Pro Gln Glu Leu Gly Ile Val Asp Lys Gln Val His
                1445                1450                1455
Ser Ser Ala Lys Arg Gly Leu Met Leu Met Ser Lys Ile Leu Gln Asn
            1460                1465                1470
```

-continued

```
Ile Ala Asn His Val Glu Phe Ser Lys Glu Gln His Met Leu Cys Phe
        1475                1480                1485
Asn Asp Phe Leu Arg Asp His Phe Glu Ala Gly Arg Arg Phe Phe Ile
        1490                1495                1500
Gln Ile Ala Ser Asp Cys Glu Thr Val Asp Gln Thr Ser His Ser Met
1505                1510                1515                1520
Ser Phe Ile Ser Asp Ala Asn Val Leu Ala Leu His Arg Leu Leu Trp
            1525                1530                1535
Thr His Gln Glu Lys Ile Gly Asp Tyr Leu Ser Ser Ser Arg Asp His
        1540                1545                1550
Lys Ala Val Gly Arg Arg Pro Phe Asp Lys Met Ala Thr Leu Leu Ala
        1555                1560                1565
Tyr Leu Gly Pro Pro Glu His Lys Pro Val Asp Ser His Met Met Phe
        1570                1575                1580
Ser Ser Tyr Ala Arg Trp Ser Ser Ile Asp Met Ser Ser Thr Asn Phe
1585                1590                1595                1600
Glu Glu Ile Met Val Lys His Gln Met His Glu Lys Glu Phe Lys
        1605                1610                1615
Thr Leu Lys Ser Met Asn Ile Phe Tyr Gln Ala Gly Thr Ser Lys Ser
        1620                1625                1630
Gly Tyr Pro Val Phe Tyr Tyr Ile Ala Arg Arg Tyr Lys Ile Gly Glu
        1635                1640                1645
Thr Asn Gly Asp Leu Leu Ile Tyr His Val Ile Leu Thr Leu Lys Pro
        1650                1655                1660
Phe Cys His Ser Pro Phe Glu Val Val Ile Asp Phe Thr His Thr Cys
1665                1670                1675                1680
Ser Asp Asn Arg Phe Arg Thr Glu Phe Leu Gln Lys Trp Phe Tyr Val
            1685                1690                1695
Leu Pro Thr Val Ala Tyr Glu Asn Val His Ala Val Tyr Ile Tyr Asn
        1700                1705                1710
Cys Asn Ser Trp Val Arg Glu Tyr Thr Lys Phe His Asp Arg Ile Leu
        1715                1720                1725
Ala Pro Leu Lys Gly Asn Arg Lys Leu Leu Phe Leu Glu Ser Pro Asn
        1730                1735                1740
Lys Leu Thr Asp Phe Ile Asp Ala Glu Gln Gln Lys Leu Pro Gly Ala
1745                1750                1755                1760
Thr Leu Ser Leu Asp Glu Asp Leu Lys Val Phe Ser Asn Ala Leu Lys
            1765                1770                1775
Leu Ser His Lys Asp Thr Lys Val Ala Ile Lys Val Gly Pro Thr Ala
        1780                1785                1790
Leu Gln Ile Thr Ser Ala Glu Lys Thr Lys Val Leu Ala His Ser Val
        1795                1800                1805
Leu Leu Asn Asp Val Tyr Tyr Ala Ser Glu Ile Glu Glu Val Cys Leu
        1810                1815                1820
Val Asp Asp Asn Gln Phe Thr Leu Ser Ile Thr Asn Glu Ser Gly Gln
1825                1830                1835                1840
Leu Ser Phe Ile His Asn Asp Cys Asp Asn Ile Val Gln Ala Ile Ile
            1845                1850                1855
His Ile Arg Asn Arg Trp Glu Leu Ser Gln Pro Asp Ser Val Thr Val
        1860                1865                1870
His Gln Lys Ile Arg Pro Lys Asp Val Pro Gly Thr Leu Leu Asn Met
        1875                1880                1885
```

```
Ala Leu Leu Asn Leu Gly Ser Cys Asp Pro Asn Leu Arg Thr Ala Ala
        1890                1895                1900
Tyr Asn Leu Leu Cys Ala Leu Thr Ala Thr Phe Asp Leu Lys Ile Glu
1905                1910                1915                1920
Gly Gln Leu Leu Glu Thr Gln Gly Leu Cys Ile Pro Ser Asn Asn Thr
                1925                1930                1935
Ile Phe Ile Lys Ser Val Ser Glu Lys Leu Ala Thr Asn Glu Pro His
            1940                1945                1950
Leu Thr Leu Glu Phe Leu Glu Glu Ser Ile Gln Gly Phe Gln Arg Thr
                1955                1960                1965
Thr Ile Glu Leu Lys His Leu Cys Leu Glu Tyr Met Thr Pro Trp Leu
        1970                1975                1980
Lys Asn Leu Val Lys Phe Cys Lys Ser Asn Asp Asp Ser Lys Lys Leu
1985                1990                1995                2000
Lys Val Ser Gln Ile Leu Asp Lys Leu Ile Asn Leu Thr Ile Asp Gln
                2005                2010                2015
Lys Glu Met Tyr Pro Ser Val Gln Ala Lys Ile Trp Gly Ser Ile Gly
            2020                2025                2030
Gln Ile Pro Glu Leu Ile Asp Met Val Leu Asp Asn Phe Leu His Lys
        2035                2040                2045
Ser Ile Thr Tyr Gly Leu Gly Ser Pro Gln Val Glu Ile Met Ala Asp
        2050                2055                2060
Thr Ala Val Ala Leu Ala Ser Ala Asn Val Gln Leu Val Ser Lys Lys
2065                2070                2075                2080
Val Ile Thr Arg Ile Cys Arg Val Met Asp Lys Ser Cys Thr Asn Pro
                2085                2090                2095
Thr Gln Tyr Leu Glu Gln His Met Met Trp Asp Asp Ile Ala Ile Leu
            2100                2105                2110
Gly Arg Tyr Leu Leu Met Leu Ser Phe Asn Asn Cys Leu Asp Val Ala
        2115                2120                2125
Thr Ser Val Pro Tyr Leu Phe His Thr Ile Thr Phe Leu Val Cys Ser
        2130                2135                2140
Gly Ser Leu Ser Met Arg Ala Ser Thr His Gly Leu Val Ile Asn Ile
2145                2150                2155                2160
Ile His Ser Leu Cys Thr Cys Thr Asn Pro Ser Phe Ser Glu Glu Ala
                2165                2170                2175
Gln Arg Val Leu Arg Leu Ser Leu Asp Glu Phe Ser Leu Pro Lys Phe
            2180                2185                2190
Tyr Leu Leu Phe Gly Ile Ser Lys Val Lys Ser Ala Ala Val Thr Ala
        2195                2200                2205
Phe Arg Ser Ser Cys Arg His Pro Thr Asp Lys Trp Leu Gly Asn Glu
        2210                2215                2220
Arg Val Thr Gln Pro Leu Pro Ala Asp Arg Glu Arg Leu Ser Leu Pro
2225                2230                2235                2240
Ser Leu Glu Val Ile Thr Asp Ala Leu Leu Glu Ile Met Glu Ala Cys
                2245                2250                2255
Met Arg Asp Val Pro Asp Cys Glu Trp Leu Asn Thr Trp Thr Ser Leu
            2260                2265                2270
Ala Arg Ser Phe Ala Phe Cys Tyr Asn Pro Ala Leu Gln Pro Arg Ala
        2275                2280                2285
Leu Ile Val Tyr Gly Cys Ile Ser Lys Ser Val Thr Asp His Glu Val
        2290                2295                2300
Lys Gln Leu Leu Arg Ile Leu Val Lys Ala Leu Glu Ser Phe Asn Asp
```

-continued

```
          2305                2310                2315                2320
Leu Ile Leu Ile Glu Ala Leu Val Met Cys Leu Thr Arg Ile Gln Pro
                2325                2330                2335
Leu Leu Arg Pro Glu Ser Pro Ile His Arg Ala Leu Phe Trp Val Ala
                2340                2345                2350
Ile Ser Val Leu Gln Leu Asp Glu Ile Thr Leu Tyr Gly Ala Gly Leu
                2355                2360                2365
Ala Leu Leu Glu Gln Asn Leu His Thr Leu Lys Ser Gln Gly Cys Phe
                2370                2375                2380
Asp Lys Lys Glu Thr Ile Ala Glu Val Met Met Lys Thr Arg Glu Lys
2385                2390                2395                2400
Leu Glu Trp His Phe Lys Gln Leu Asp His Ala Val Gly Leu Ser Phe
                2405                2410                2415
Arg Ser Asn Phe His Phe Ala Leu Val Gly His Leu Ile Lys Gly Phe
                2420                2425                2430
Arg His Pro Thr Pro Thr Thr Val Ser Arg Thr Ser Arg Val Leu Thr
                2435                2440                2445
Met Leu Leu Gly Ile Tyr Ala Lys Pro Leu His Arg Asp Lys Phe Glu
                2450                2455                2460
Val Thr Pro Asp Ser Val Ala Tyr Leu Thr Ala Leu Val Ala Val Ser
2465                2470                2475                2480
Glu Glu Val Arg Ser Arg Cys His Val Lys His Ala Leu Pro Arg Trp
                2485                2490                2495
Pro Ala Asp Leu Ser Ser Ser Val Glu Asn Gly Glu Ala Ser Gly Gly
                2500                2505                2510
Val Gln Ala Ile Gly Leu Pro Leu Ser Arg Arg Gln Lys Ser Trp Asp
                2515                2520                2525
Ile Leu Asp Gln Ser Ala Leu Gln Phe Ala Arg Gln His Lys Val Pro
                2530                2535                2540
Thr Leu Gln Asn Ala Arg Val Leu Phe Lys Thr Gln Arg Ser Phe Ser
2545                2550                2555                2560
Val Pro Thr Thr Lys Asp Pro Asn Asn Ala Thr Gly Ile Glu Glu Arg
                2565                2570                2575
Gln Glu Arg Gly Ser Arg Ser Ser Val Ser Asn Glu Ser Asn Val Leu
                2580                2585                2590
Leu Asp Pro Glu Val Leu Pro Asp Leu Ser Ile Gln Ala Leu Val Leu
                2595                2600                2605
Thr Val Leu Ala Thr Leu Val Lys Tyr Ser Ser Asp Glu Gly Glu Thr
                2610                2615                2620
Arg Val Leu Tyr Gln Tyr Leu Ala Glu Gly Ser Val Val Phe Pro Lys
2625                2630                2635                2640
Val Phe Pro Val Ile His Ser Leu Leu Asp Gln Lys Ile Asn Asn Ile
                2645                2650                2655
Leu Ser Val Ser His Asp Gln Val Val Leu Asn Ser Val Gln Asn Ile
                2660                2665                2670
Ile Gln Asn Met Leu Ala Ser Glu Asp Pro Ser Gln Gln Leu His
                2675                2680                2685
Phe Leu Gln Ser Cys Gly Phe Gly Gly Leu Trp Arg Phe Ala Gly Pro
                2690                2695                2700
Phe Thr Lys Tyr Asn Met Met Gly Glu Ser Ser Glu Leu Phe Val Asn
2705                2710                2715                2720
Cys Leu Glu Ala Met Val Glu Thr Cys Leu Pro Gly Asp Glu Ser Ala
                2725                2730                2735
```

```
Pro Val Pro Pro Ser Pro Arg Pro Tyr Asn Leu Ser Ser Leu Ser
            2740            2745                2750

Ser Leu Thr Leu Gly Ser Pro Thr Asp Lys Ala Phe Ser Ser Glu Ser
            2755                2760                2765

Leu Asp Phe Tyr Asp Asn Cys Pro Gly Ser Val Ser Ser Leu Arg Arg
            2770                2775                2780

Ala Ser His Ser Lys Ser Arg Ala Lys His Arg Ile Asn Asp Ser Pro
2785                2790                2795                2800

Ser His

<210> SEQ ID NO 2
<211> LENGTH: 2818
<212> TYPE: PRT
<213> ORGANISM: Human

<400> SEQUENCE: 2

Met Ala Ala His Arg Pro Val Glu Trp Val Gln Ala Val Val Ser Arg
 1               5                  10                  15

Phe Asp Glu Gln Leu Pro Ile Lys Thr Gly Gln Gln Asn Thr His Thr
            20                  25                  30

Lys Val Ser Thr Glu His Asn Lys Glu Cys Leu Ile Asn Ile Ser Lys
            35                  40                  45

Tyr Lys Phe Ser Leu Val Ile Ser Gly Leu Thr Thr Ile Leu Lys Asn
 50                  55                  60

Val Asn Asn Met Arg Ile Phe Gly Glu Ala Ala Glu Lys Asn Leu Tyr
 65                  70                  75                  80

Leu Ser Gln Leu Ile Ile Leu Asp Thr Leu Glu Lys Cys Leu Ala Gly
                85                  90                  95

Gln Pro Lys Asp Thr Met Arg Leu Asp Glu Thr Met Leu Val Lys Gln
            100                 105                 110

Leu Leu Pro Glu Ile Cys His Phe Leu His Thr Cys Arg Glu Gly Asn
            115                 120                 125

Gln His Ala Ala Glu Leu Arg Asn Ser Ala Ser Gly Val Leu Phe Ser
        130                 135                 140

Leu Ser Cys Asn Asn Phe Asn Ala Val Phe Ser Arg Ile Ser Thr Arg
145                 150                 155                 160

Leu Gln Glu Leu Thr Val Cys Ser Glu Asp Asn Val Asp Val His Asp
                165                 170                 175

Ile Glu Leu Leu Gln Tyr Ile Asn Val Asp Cys Ala Lys Leu Lys Arg
            180                 185                 190

Leu Leu Lys Glu Thr Ala Phe Lys Phe Lys Ala Leu Lys Lys Val Ala
            195                 200                 205

Gln Leu Ala Val Ile Asn Ser Leu Glu Lys Ala Phe Trp Asn Trp Val
        210                 215                 220

Glu Asn Tyr Pro Asp Glu Phe Thr Lys Leu Tyr Gln Ile Pro Gln Thr
225                 230                 235                 240

Asp Met Ala Glu Cys Ala Glu Lys Leu Phe Asp Leu Val Asp Gly Phe
                245                 250                 255

Ala Glu Ser Thr Lys Arg Lys Ala Ala Val Trp Pro Leu Gln Ile Ile
            260                 265                 270

Leu Leu Ile Leu Cys Pro Glu Ile Ile Gln Asp Ile Ser Lys Asp Val
            275                 280                 285

Val Asp Glu Asn Asn Met Asn Lys Lys Leu Phe Leu Asp Ser Leu Arg
        290                 295                 300
```

```
Lys Ala Leu Ala Gly His Gly Gly Ser Arg Gln Leu Thr Glu Ser Ala
305                 310                 315                 320

Ala Ile Ala Cys Val Lys Leu Cys Lys Ala Ser Thr Tyr Ile Asn Trp
            325                 330                 335

Glu Asp Asn Ser Val Ile Phe Leu Leu Val Gln Ser Met Val Val Asp
            340                 345                 350

Leu Lys Asn Leu Leu Phe Asn Pro Ser Lys Pro Phe Ser Arg Gly Ser
            355                 360                 365

Gln Pro Ala Asp Val Asp Leu Met Ile Asp Cys Leu Val Ser Cys Phe
            370                 375                 380

Arg Ile Ser Pro His Asn Asn Gln His Phe Lys Ile Cys Leu Ala Gln
385                 390                 395                 400

Asn Ser Pro Ser Thr Phe His Tyr Val Leu Val Asn Ser Leu His Arg
                405                 410                 415

Ile Ile Thr Asn Ser Ala Leu Asp Trp Trp Pro Lys Ile Asp Ala Val
            420                 425                 430

Tyr Cys His Ser Val Glu Leu Arg Asn Met Phe Gly Glu Thr Leu His
            435                 440                 445

Lys Ala Val Gln Gly Cys Gly Ala His Pro Ala Ile Arg Met Ala Pro
450                 455                 460

Ser Leu Thr Phe Lys Glu Lys Val Thr Ser Leu Lys Phe Lys Glu Lys
465                 470                 475                 480

Pro Thr Asp Leu Glu Thr Arg Ser Tyr Lys Tyr Leu Leu Leu Ser Met
                485                 490                 495

Val Lys Leu Ile His Ala Asp Pro Lys Leu Leu Leu Cys Asn Pro Arg
            500                 505                 510

Lys Gln Gly Pro Glu Thr Gln Gly Ser Thr Ala Glu Leu Ile Thr Gly
            515                 520                 525

Leu Val Gln Leu Val Pro Gln Ser His Met Pro Glu Ile Ala Gln Glu
            530                 535                 540

Ala Met Glu Ala Leu Leu Val Leu His Gln Leu Asp Ser Ile Asp Leu
545                 550                 555                 560

Trp Asn Pro Asp Ala Pro Val Glu Thr Phe Trp Glu Ile Ser Ser Gln
            565                 570                 575

Met Leu Phe Tyr Ile Cys Lys Lys Leu Thr Ser His Gln Met Leu Ser
            580                 585                 590

Ser Thr Glu Ile Leu Lys Trp Leu Arg Glu Ile Leu Ile Cys Arg Asn
            595                 600                 605

Lys Phe Leu Leu Lys Asn Lys Gln Ala Asp Arg Ser Ser Cys His Phe
            610                 615                 620

Leu Leu Phe Tyr Gly Val Gly Cys Asp Ile Pro Ser Ser Gly Asn Thr
625                 630                 635                 640

Ser Gln Met Ser Met Asp His Glu Glu Leu Leu Arg Thr Pro Gly Ala
                645                 650                 655

Ser Leu Arg Lys Gly Lys Gly Asn Ser Ser Met Asp Ser Ala Ala Cys
            660                 665                 670

Cys Ser Gly Thr Pro Pro Ile Cys Arg Gln Ala Gln Thr Lys Leu Glu
            675                 680                 685

Val Ala Leu Tyr Met Phe Leu Trp Asn Pro Asp Thr Glu Ala Val Leu
            690                 695                 700

Val Ala Met Ser Cys Phe Arg His Leu Cys Glu Glu Ala Asp Ile Arg
705                 710                 715                 720
```

-continued

```
Cys Gly Val Asp Glu Val Ser Val His Asn Leu Leu Pro Asn Tyr Asn
            725                 730                 735

Thr Phe Met Glu Phe Ala Ser Val Ser Asn Met Met Ser Thr Gly Arg
            740                 745                 750

Ala Ala Leu Gln Lys Arg Val Met Ala Leu Leu Arg Arg Ile Glu His
            755                 760                 765

Pro Thr Ala Gly Asn Thr Glu Ala Trp Glu Asp Thr His Ala Lys Trp
            770                 775                 780

Glu Gln Ala Thr Lys Leu Ile Leu Asn Tyr Pro Lys Ala Lys Met Glu
785                 790                 795                 800

Asp Gly Gln Ala Ala Glu Ser Leu His Lys Thr Ile Val Lys Arg Arg
            805                 810                 815

Met Ser His Val Ser Gly Gly Ser Ile Asp Leu Ser Asp Thr Asp
            820                 825                 830

Ser Leu Gln Glu Trp Ile Asn Met Thr Gly Phe Leu Cys Ala Leu Gly
            835                 840                 845

Gly Val Cys Leu Gln Gln Arg Ser Asn Ser Gly Leu Ala Thr Tyr Ser
            850                 855                 860

Pro Pro Met Gly Pro Val Ser Glu Arg Lys Gly Ser Met Ile Ser Val
865                 870                 875                 880

Met Ser Ser Glu Gly Asn Ala Asp Thr Pro Val Ser Lys Phe Met Asp
            885                 890                 895

Arg Leu Leu Ser Leu Met Val Cys Asn His Glu Lys Val Gly Leu Gln
            900                 905                 910

Ile Arg Thr Asn Val Lys Asp Leu Val Gly Leu Glu Leu Ser Pro Ala
            915                 920                 925

Leu Tyr Pro Met Leu Phe Asn Lys Leu Lys Asn Thr Ile Ser Lys Phe
            930                 935                 940

Phe Asp Ser Gln Gly Gln Val Leu Leu Thr Asp Thr Asn Thr Gln Phe
945                 950                 955                 960

Val Glu Gln Thr Ile Ala Ile Met Lys Asn Leu Leu Asp Asn His Thr
            965                 970                 975

Glu Gly Ser Ser Glu His Leu Gly Gln Ala Ser Ile Glu Thr Met Met
            980                 985                 990

Leu Asn Leu Val Arg Tyr Val Arg Val Leu Gly Asn Met Val His Ala
            995                 1000                1005

Ile Gln Ile Lys Thr Lys Leu Cys Gln Leu Val Glu Val Met Met Ala
            1010                1015                1020

Arg Arg Asp Asp Leu Ser Phe Cys Gln Glu Met Lys Phe Arg Asn Lys
1025                1030                1035                1040

Met Val Glu Tyr Leu Thr Asp Trp Val Met Gly Thr Ser Asn Gln Ala
            1045                1050                1055

Ala Asp Asp Val Lys Cys Leu Thr Arg Asp Leu Asp Gln Ala Ser
            1060                1065                1070

Met Glu Ala Val Val Ser Leu Leu Ala Gly Leu Pro Leu Gln Pro Glu
            1075                1080                1085

Glu Gly Asp Gly Val Glu Leu Met Glu Ala Lys Ser Gln Leu Phe Leu
            1090                1095                1100

Lys Tyr Phe Thr Leu Phe Met Asn Leu Leu Asn Asp Cys Ser Glu Val
1105                1110                1115                1120

Glu Asp Glu Ser Ala Gln Thr Gly Gly Arg Lys Arg Gly Met Ser Arg
            1125                1130                1135

Arg Leu Ala Ser Leu Arg His Cys Thr Val Leu Ala Met Ser Asn Leu
```

-continued

```
                   1140              1145              1150
Leu Asn Ala Asn Val Asp Ser Gly Leu Met His Ser Ile Gly Leu Gly
        1155              1160              1165

Tyr His Lys Asp Leu Gln Thr Arg Ala Thr Phe Met Glu Val Leu Thr
1170              1175              1180

Lys Ile Leu Gln Gln Gly Thr Glu Phe Asp Thr Leu Ala Glu Thr Val
1185              1190              1195              1200

Leu Ala Asp Arg Phe Glu Arg Leu Val Glu Leu Val Ile Met Met Gly
            1205              1210              1215

Asp Gln Gly Glu Leu Pro Ile Ala Met Ala Leu Ala Asn Val Val Pro
        1220              1225              1230

Cys Ser Gln Trp Asp Glu Leu Ala Arg Val Leu Val Thr Leu Phe Asp
        1235              1240              1245

Ser Arg His Leu Leu Tyr Gln Leu Leu Trp Asn Met Phe Ser Lys Glu
        1250              1255              1260

Val Glu Leu Ala Asp Ser Met Gln Thr Leu Phe Arg Gly Asn Ser Leu
1265              1270              1275              1280

Ala Ser Lys Ile Met Thr Phe Cys Phe Lys Val Tyr Gly Ala Thr Tyr
            1285              1290              1295

Leu Gln Lys Leu Leu Asp Pro Leu Leu Arg Ile Val Ile Thr Ser Ser
            1300              1305              1310

Asp Trp Gln His Val Ser Phe Glu Val Asp Pro Thr Arg Leu Glu Pro
            1315              1320              1325

Ser Glu Ser Leu Glu Glu Asn Gln Arg Asn Leu Leu Gln His Thr Glu
        1330              1335              1340

Lys Phe Phe His Ala Ile Ile Ser Ser Ser Glu Phe Pro Pro Gln
1345              1350              1355              1360

Leu Arg Ser Val Cys His Cys Leu Tyr Gln Val Val Ser Gln Arg Phe
            1365              1370              1375

Pro Gln Asn Ser Ile Gly Ala Val Gly Ser Ala Met Phe Leu Arg Phe
            1380              1385              1390

Ile Asn Pro Ala Ile Val Ser Pro Tyr Glu Ala Gly Ile Leu Asp Lys
            1395              1400              1405

Lys Pro Pro Pro Arg Ile Glu Arg Gly Leu Lys Leu Met Ser Lys Ile
        1410              1415              1420

Leu Gln Ser Ile Ala Asn His Val Leu Phe Thr Lys Glu Glu His Met
1425              1430              1435              1440

Arg Pro Phe Asn Asp Phe Val Lys Ser Asn Phe Asp Ala Ala Arg Arg
            1445              1450              1455

Phe Phe Leu Asp Ile Ala Ser Asp Cys Pro Thr Ser Asp Ala Val Asn
            1460              1465              1470

His Ser Leu Ser Phe Ile Ser Asp Gly Asn Val Leu Ala Leu His Arg
        1475              1480              1485

Leu Leu Trp Asn Asn Gln Glu Lys Ile Gly Gln Tyr Leu Ser Ser Asn
        1490              1495              1500

Arg Asp His Lys Ala Val Gly Arg Arg Pro Phe Asp Lys Met Ala Thr
1505              1510              1515              1520

Leu Leu Ala Tyr Leu Gly Pro Pro Glu His Lys Pro Val Ala Asp Thr
            1525              1530              1535

His Trp Ser Ser Leu Asn Leu Thr Ser Ser Lys Phe Glu Glu Phe Met
            1540              1545              1550

Thr Arg His Gln Val His Glu Lys Glu Glu Phe Lys Ala Leu Lys Thr
        1555              1560              1565
```

-continued

```
Leu Ser Ile Phe Tyr Gln Ala Gly Thr Ser Lys Ala Gly Asn Pro Ile
    1570                1575                1580

Phe Tyr Tyr Val Ala Arg Arg Phe Lys Thr Gly Gln Ile Asn Gly Asp
1585                1590                1595                1600

Leu Leu Ile Tyr His Val Leu Leu Thr Leu Lys Pro Tyr Tyr Ala Lys
                1605                1610                1615

Pro Tyr Glu Ile Val Val Asp Leu Thr His Thr Gly Pro Ser Asn Arg
            1620                1625                1630

Phe Lys Thr Asp Phe Leu Ser Lys Trp Phe Val Val Phe Pro Gly Phe
            1635                1640                1645

Ala Tyr Asp Asn Val Ser Ala Val Tyr Ile Tyr Asn Cys Asn Ser Trp
            1650                1655                1660

Val Arg Glu Tyr Thr Lys Tyr His Glu Arg Leu Leu Thr Gly Leu Lys
1665                1670                1675                1680

Gly Ser Lys Arg Leu Val Phe Ile Asp Cys Pro Gly Lys Leu Ala Glu
                1685                1690                1695

His Ile Glu His Glu Gln Gln Lys Leu Pro Ala Ala Thr Leu Ala Leu
            1700                1705                1710

Glu Glu Asp Leu Lys Val Phe His Asn Ala Leu Lys Leu Ala His Lys
            1715                1720                1725

Asp Thr Lys Val Ser Ile Lys Val Gly Ser Thr Ala Val Gln Val Thr
            1730                1735                1740

Ser Ala Glu Arg Thr Lys Val Leu Gly Gln Ser Val Phe Leu Asn Asp
1745                1750                1755                1760

Ile Tyr Tyr Ala Ser Glu Ile Glu Glu Ile Cys Leu Val Asp Glu Asn
                1765                1770                1775

Gln Phe Thr Leu Thr Ile Ala Asn Gln Gly Thr Pro Leu Thr Phe Met
            1780                1785                1790

His Gln Glu Cys Glu Ala Ile Val Gln Ser Ile Ile His Ile Arg Thr
            1795                1800                1805

Arg Trp Glu Leu Ser Gln Pro Asp Ser Ile Pro Gln His Thr Lys Ile
            1810                1815                1820

Arg Pro Lys Asp Val Pro Gly Thr Leu Leu Asn Ile Ala Leu Leu Asn
1825                1830                1835                1840

Leu Gly Ser Ser Asp Pro Ser Leu Arg Ser Ala Ala Tyr Asn Leu Leu
                1845                1850                1855

Cys Ala Leu Thr Cys Thr Phe Asn Leu Lys Ile Glu Gly Gln Leu Leu
            1860                1865                1870

Glu Thr Ser Gly Leu Cys Ile Pro Ala Asn Asn Thr Leu Phe Ile Val
            1875                1880                1885

Ser Ile Ser Lys Thr Leu Ala Ala Asn Glu Pro His Leu Thr Leu Glu
    1890                1895                1900

Phe Leu Glu Glu Cys Ile Ser Gly Phe Ser Lys Ser Ser Ile Glu Leu
1905                1910                1915                1920

Lys His Leu Cys Leu Glu Tyr Met Thr Pro Trp Leu Ser Asn Leu Val
                1925                1930                1935

Arg Phe Cys Lys His Asn Asp Asp Ala Lys Arg Gln Arg Val Thr Ala
            1940                1945                1950

Ile Leu Asp Lys Leu Ile Thr Met Thr Ile Asn Glu Lys Gln Met Tyr
            1955                1960                1965

Pro Ser Ile Gln Ala Lys Ile Trp Gly Ser Leu Gly Gln Ile Thr Asp
    1970                1975                1980
```

-continued

```
Leu Leu Asp Val Val Leu Asp Ser Phe Ile Lys Thr Ser Ala Thr Gly
1985                1990                1995                2000

Gly Leu Gly Ser Ile Lys Ala Glu Val Met Ala Asp Thr Ala Val Ala
                2005                2010                2015

Leu Ala Ser Gly Asn Val Lys Leu Val Ser Ser Lys Val Ile Gly Arg
                2020                2025                2030

Met Cys Lys Ile Ile Asp Lys Thr Cys Leu Ser Pro Thr Pro Thr Leu
                2035                2040                2045

Glu Gln His Leu Met Trp Asp Asp Ile Ala Ile Leu Ala Arg Tyr Met
                2050                2055                2060

Leu Met Leu Ser Phe Asn Asn Ser Leu Asp Val Ala Ala His Leu Pro
2065                2070                2075                2080

Tyr Leu Phe His Val Val Thr Phe Leu Val Ala Thr Gly Pro Leu Ser
                2085                2090                2095

Leu Arg Ala Ser Thr His Gly Leu Val Ile Asn Ile Ile His Ser Leu
                2100                2105                2110

Cys Thr Cys Ser Gln Leu His Phe Ser Glu Thr Lys Gln Val Leu
                2115                2120                2125

Arg Leu Ser Leu Thr Glu Phe Ser Leu Pro Lys Phe Tyr Leu Leu Phe
                2130                2135                2140

Gly Ile Ser Lys Val Lys Ser Ala Ala Val Ile Ala Phe Arg Ser Ser
2145                2150                2155                2160

Tyr Arg Asp Arg Ser Phe Ser Pro Gly Ser Tyr Glu Arg Glu Thr Phe
                2165                2170                2175

Ala Leu Thr Ser Leu Glu Thr Val Thr Glu Ala Leu Leu Glu Ile Met
                2180                2185                2190

Glu Ala Cys Met Arg Asp Ile Pro Thr Cys Lys Trp Leu Asp Gln Trp
                2195                2200                2205

Thr Glu Leu Ala Gln Arg Phe Ala Phe Gln Tyr Asn Pro Ser Leu Gln
                2210                2215                2220

Pro Arg Ala Leu Val Val Phe Gly Cys Ile Ser Lys Arg Val Ser His
2225                2230                2235                2240

Gly Gln Ile Lys Gln Ile Ile Arg Ile Leu Ser Lys Ala Leu Glu Ser
                2245                2250                2255

Cys Leu Lys Gly Pro Asp Thr Tyr Asn Ser Gln Val Leu Ile Glu Ala
                2260                2265                2270

Thr Val Ile Ala Leu Thr Lys Leu Gln Pro Leu Leu Asn Lys Asp Ser
                2275                2280                2285

Pro Leu His Lys Ala Leu Phe Trp Val Ala Val Ala Val Leu Gln Leu
                2290                2295                2300

Asp Glu Val Asn Leu Tyr Ser Ala Gly Thr Ala Leu Leu Glu Gln Asn
2305                2310                2315                2320

Leu His Thr Leu Asp Ser Leu Arg Ile Phe Asn Asp Lys Ser Pro Glu
                2325                2330                2335

Glu Val Phe Met Ala Ile Arg Asn Pro Leu Glu Trp His Cys Lys Gln
                2340                2345                2350

Met Asp His Phe Val Gly Leu Asn Phe Asn Ser Asn Phe Asn Phe Ala
                2355                2360                2365

Leu Val Gly His Leu Leu Lys Gly Tyr Arg His Pro Ser Pro Ala Ile
                2370                2375                2380

Val Ala Arg Thr Val Arg Ile Leu His Thr Leu Leu Thr Leu Val Asn
2385                2390                2395                2400

Lys His Arg Asn Cys Asp Lys Phe Glu Val Asn Thr Gln Ser Val Ala
```

-continued

```
                2405                2410                2415
Tyr Leu Ala Ala Leu Leu Thr Val Ser Glu Glu Val Arg Ser Arg Cys
                2420                2425                2430
Ser Leu Lys His Arg Lys Ser Leu Leu Leu Thr Asp Ile Ser Met Glu
        2435                2440                2445
Asn Val Pro Met Asp Thr Tyr Pro Ile His His Gly Asp Pro Ser Tyr
    2450                2455                2460
Arg Thr Leu Lys Glu Thr Gln Pro Trp Ser Ser Pro Lys Gly Ser Glu
2465                2470                2475                2480
Gly Tyr Leu Ala Ala Thr Tyr Pro Thr Val Gly Gln Thr Ser Pro Arg
                2485                2490                2495
Ala Arg Lys Ser Met Ser Leu Asp Met Gly Gln Pro Ser Gln Ala Asn
            2500                2505                2510
Thr Lys Lys Leu Leu Gly Thr Arg Lys Ser Phe Asp His Leu Ile Ser
        2515                2520                2525
Asp Thr Lys Ala Pro Lys Arg Gln Glu Met Glu Ser Gly Ile Thr Thr
    2530                2535                2540
Pro Pro Lys Met Arg Arg Val Ala Glu Thr Asp Tyr Glu Met Glu Thr
2545                2550                2555                2560
Gln Arg Ile Ser Ser Ser Gln Gln His Pro His Leu Arg Lys Val Ser
                2565                2570                2575
Val Ser Glu Ser Asn Val Leu Leu Asp Glu Glu Val Leu Thr Asp Pro
            2580                2585                2590
Lys Ile Gln Ala Leu Leu Leu Thr Val Leu Ala Thr Leu Val Lys Tyr
        2595                2600                2605
Thr Thr Asp Glu Phe Asp Gln Arg Ile Leu Tyr Glu Tyr Leu Ala Glu
    2610                2615                2620
Ala Ser Val Val Phe Pro Lys Val Phe Pro Val Val His Asn Leu Leu
2625                2630                2635                2640
Asp Ser Lys Ile Asn Thr Leu Leu Ser Leu Cys Gln Asp Pro Asn Leu
                2645                2650                2655
Leu Asn Pro Ile His Gly Ile Val Gln Ser Val Val Tyr His Glu Glu
            2660                2665                2670
Ser Pro Pro Gln Tyr Gln Thr Ser Tyr Leu Gln Ser Phe Gly Phe Asn
        2675                2680                2685
Gly Leu Trp Arg Phe Ala Gly Pro Phe Ser Lys Gln Thr Gln Ile Pro
    2690                2695                2700
Asp Tyr Ala Glu Leu Ile Val Lys Phe Leu Asp Ala Leu Ile Asp Thr
2705                2710                2715                2720
Tyr Leu Pro Gly Ile Asp Glu Glu Thr Ser Glu Glu Ser Leu Leu Thr
                2725                2730                2735
Pro Thr Ser Pro Tyr Pro Pro Ala Leu Gln Ser Gln Leu Ser Ile Thr
            2740                2745                2750
Ala Asn Leu Asn Leu Ser Asn Ser Met Thr Ser Leu Ala Thr Ser Gln
        2755                2760                2765
His Ser Pro Gly Ile Asp Lys Glu Asn Val Glu Leu Ser Pro Thr Thr
    2770                2775                2780
Gly His Cys Asn Ser Gly Arg Thr Arg His Gly Ser Ala Ser Gln Val
2785                2790                2795                2800
Gln Lys Gln Arg Ser Ala Gly Ser Phe Lys Arg Asn Ser Ile Lys Lys
                2805                2810                2815
Ile Val
```

```
<210> SEQ ID NO 3
<211> LENGTH: 6
<212> TYPE: PRT
<213> ORGANISM: Drosophila

<400> SEQUENCE: 3

Pro Thr Asp Lys Ala Ala
 1               5
```

NF1 PROTEIN AND ITS ROLE IN ACTIVATION OF ADENYLYL CYCLASE BY PACAP38-LIKE NEUROPEPTIDES

RELATED APPLICATIONS

This application is a Continuation of U.S. application Ser. No.: 09/046,745, filed on Mar. 24, 1998, now abandoned, which claims the benefit of U.S. Provisional Application Serial No. 60/041,469, which was filed on Mar. 24, 1997, the entire teachings of which are incorporated herein by reference.

BACKGROUND OF THE INVENTION

Mutations in the ncurofibromatosis type 1 gene (NF1) lead to a common genetic disorder that is identified by benign tumors of the peripheral nerves, hyperpigmentation, white matter lesions in the brain, learning disabilities, and many other manifestations (D. Viskochil et al., *Annu. Rev. Neurosci.* 16:183 (1993); F. McCormick, *Curr. Opinion Genet. Dev.* 5:51–55 (1995); K. North et al., Neurology 44:878 (1994)). The NF1 protein, which contains a fragment similar to the GTPase activating protein for Ras (Ras-GAP), stimulates the intrinsic activity of Ras-GTPase and therefore inhibits biological activation of Ras (G. F. Xu, et al., *Cell* 62:599 (1990); *Cell* 63:835 (1990); A. M. Buchberg etal., *Nature* 347.291 (1990); R. Ballester etal., *Cell* 63.851 (1990); G. A. Martin et al., *Cell* 63:843 (1990)).

The gene responsible for human neurofibromatosis type 1 (NF1) encodes a large protein that contains a central domain related to RasGAPs (S. M. Huson, et al., *Brain* 111:1355–1381 (1988); F. McCormick, *Curr. Opin. Gen. Dev.* 5:51–55 (1995); A. Bernards, Biochem. *Biophys. Acta* 1242:43–60 (1995)). Loss of NF1 expression correlates with increased Ras activity in several mammalian tumor cell types (T. N. Basu, et al., *Nature* 356:713–715 (1992); J. E. DeClue, et al., *Cell* 69:265–273 (1992); H. A. Kim et al., *Oncogene* 11:325–35 (1995); G. Bollag, et al., *Nat. Genet.* 12:144–8 (1996); D. A. Largaespada et al., *Nat. Genet.* 12:137–143 (1996)). However, the precise signaling pathways regulated by the NF1 protein remain poorly understood. Identification of such pathways would help to define molecular mechanisms underlying the extremely diverse symptoms observed in NF1 patients, which in addition to frequent benign and infrequent malignant tumors also include short stature and learning disabilities (S. M. Huson et al., *Brain* 111:1355–1381 (1988); F. McCormick, *Curr. Opin. Gen. Dev.* 5:51–55 (1995); A. Bernards, *Biochim. Biophys.* Acta 1242:43–60 (1995)).

SUMMARY OF THE INVENTION

In one aspect of the present invention, diseases associated with a defect in the NF1 protein are prevented. These diseases include neurofibromatosis type 1, benign tumors, malignant tumors, short stature, hyperpigmentation, white matter lesions in the brain and learning disabilities. The NF1 protein defect is either a diminution in the amount of NF1 protein produced, a diminution in the activity of the NF1 protein produced or both a diminution in amount and activity of NF1 protein. The diseases are prevented by the administration of the NF1 protein, or biologically active homolog, itself or an inducible gene which codes for either the NF1 protein or a biologically active homolog of the NF1 protein.

In another aspect of the present invention, an assessment can be made of whether diseases are associated with a defect in the NF1 protein by measuring the production of cAMP in tissue from an individual that exhibits one or more of the diseases. An NF1 protein defect is manifested by a loss of cAMP formation. This loss can be measured directly or, alternatively, by determining the lack of activity of protein kinase A (PKA) which is activated by cAMP.

In still another aspect of the present invention, the ability of a given compound to induce the production of cAMP can be determined by incubating the compound with two separate cellular preparations that differ from each other by the functional NF1 protein content. In one cellular preparation, functional NF1 protein is present; in the second preparation, NF1 protein is either absent or it is inactive. If a difference is noted in the amount of cAMP produced by the two preparations, with the preparation containing functional NF1 protein producing more cAMP than the preparation lacking functional NF1 protein, the compound can be categorized as having the property of inducing the production of cAMP.

BRIEF DESCRIPTION OF THE DRAWINGS

FIG. 2 is a pictorial representation of the amino acid alignment of the Drosophila and human NF1 proteins. (SEQ ID NO: 1 and SEQ NO: 2)

DETAILED DESCRIPTION OF THE INVENTION

The neurofibromatosis type 1 (NF1) tumor suppressor gene product is believed to restrict cell proliferation by functioning as a Ras-specific GTPase activating protein (RasGAP). However, upon generating homozygous null mutations in a Drosophila NF1 homolog, no evidence of perturbed Rasl-mediated signaling was found, even in genetic backgrounds that reveal subtle abnormalities in Ras pathway function. Loss of NF1 causes mutants to be reduced in size and mutants also exhibit a diminished escape response. The size defect of NF1 mutants is not modified by manipulating Ras1 signaling, but is rescued by increased cyclic AMP (cAMP)-dependent protein kinase A (PKA) activity. Moreover, mutations that reduce PKA levels phenocopy NF1 mutations. These observations suggest that NF1 and PKA interact in a pathway that controls the overall growth of the organism.

The NF1 protein does not act solely to regulate Ras, but also functions as an effector mediating signaling important for differentiation. The present study of Drosophila NF1 mutants indicates that the activation of rutabaga (rut)-encoded adenylyl cyclase (M. S. Livingstone et al., *Cell* 37:205 (1984); L. R. Levin et al., *Cell* 68:479 (1992)) through heterotrimeric guanine nucleotide binding protein (G protein)-coupled receptors is regulated by the NF1 protein.

As described herein, a highly conserved Drosophila homolog of the human NF1 tumor suppressor gene has been characterized. Molecular and genetic analysis of this gene has resulted in four observations that are relevant to the study of human NF1 function. Firstly, the Drosophila NF1 protein is similar to mammalian neurofibromin over its entire length, suggesting that additional functional domains reside outside the centrally located GAP- and IRA-related segments. Secondly, the reduced size of NF1 deficient flies reflects a non-autonomous requirement for NF1, suggesting that some human NF1 symptoms may also have non-cell autonomous origins. It should be noted in this respect that a short stature is among the most common symptoms of NF1, found in approximately 30% of patients (S. M. Huson, et al., *Brain* 111:1355–1381 (1988); F. McCormick, *Curr. Opin. Gen. Dev.* 5:51–55 (1995); A. Bernards, *Biochem. Biophys. Acta* 1242:43–60 (1995)). Thirdly, Ras1-mediated signals downstream of at least two receptor tyrosine kinases are not detectably perturbed by the complete absence of NF1. The size and behavioral phenotypes of NF1 mutants may thus reflect roles for NF1 in Ras1-mediated pathways downstream of other receptor types, e.g., G protein-coupled receptors, or even reflect functions for NF1 unrelated to its role as a Ras regulator. Finally and most intriguingly, the size defect of NF1 mutants is not modified by manipulating Ras1 pathway components, but is mimicked by reducing PKA levels and rescued by increasing PKA activity. If NF1 and PKA do indeed function in the same pathway, one possibility is that NF1 regulates PKA activity.

Figure 1A:
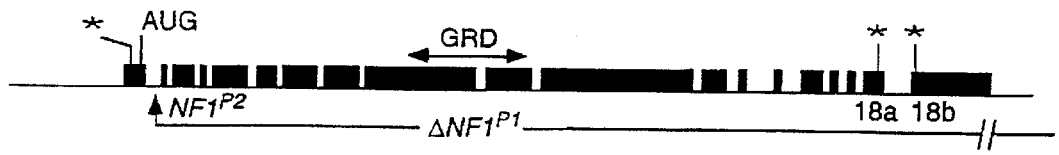
FIG. 1A is a graphical representation of the Drosophila NF1 gene.
Figure 1B:
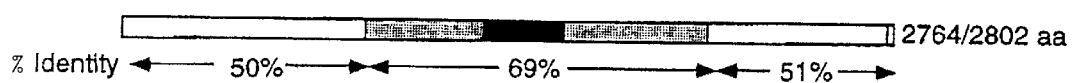
FIG. 1B is a diagram representation of the percentage amino acid identity between Drosophila and human NF1 segments.
Figure 2:
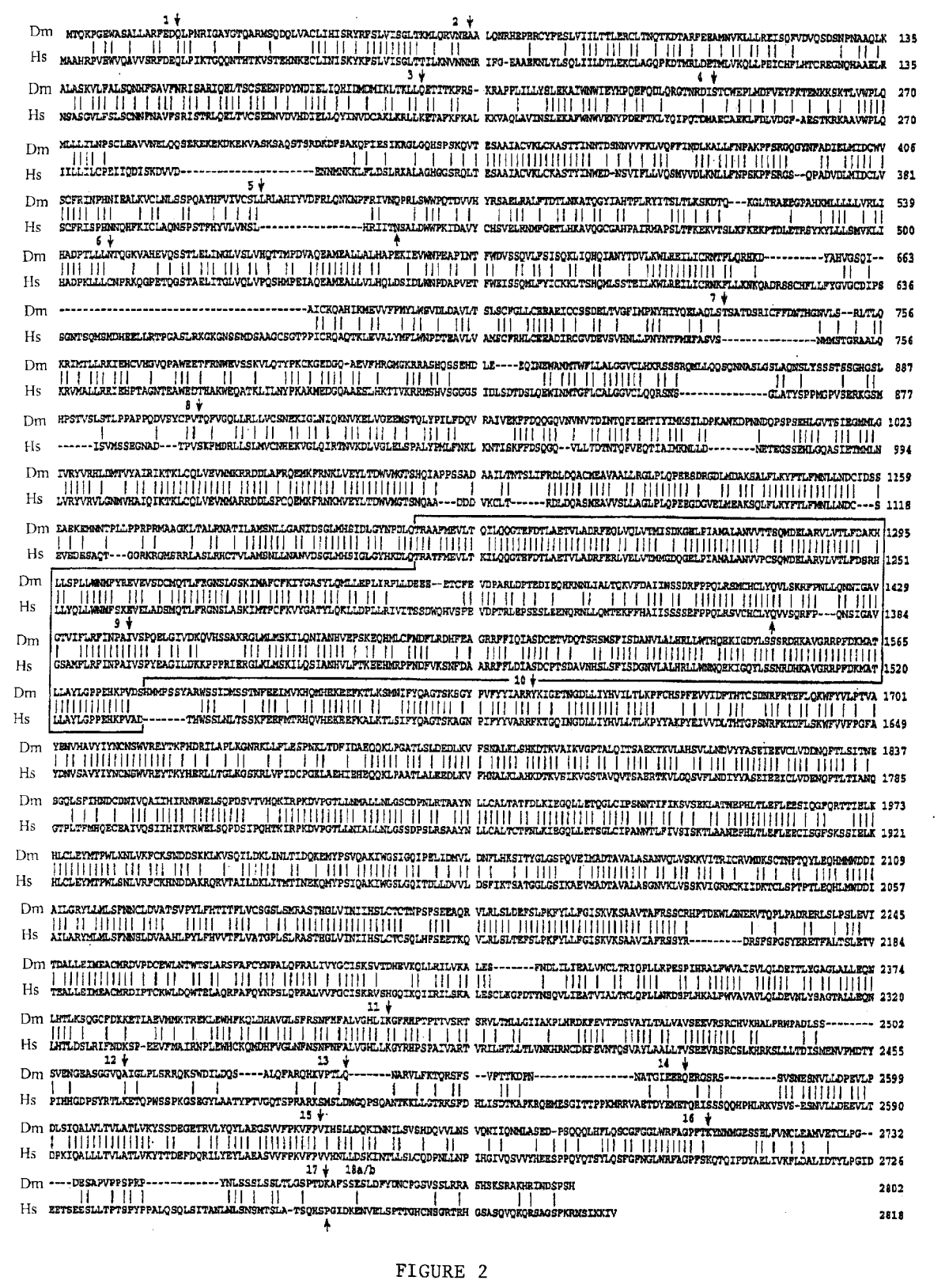

FIGS. 1A, 1B and 2 show the Drosophila NF1 gene structure and comparison of the encoded protein to human neurofibromin. FIG. 1A shows the intron-exon structure and location of translational start and stop codons. The location of a P-element in $NF1^{P2}$ and the extent of the deletion in $NF1^{P1}$ are indicated. FIG. 1B shows the percentage amino acid sequence identity between the indicated segments of Drosophila and human NF1. The GRD and IRA-related segments are drawn as black and shaded boxes, respectively. FIG. 2 shows the alignment of Drosophila (Dm) and human (Hs) NF1 proteins. Dashes were introduced to optimize the alignment. Amino acids encoded by the last complete codon in each exon are labeled with ◇ signs. The boxed segment shows the approximate extent of the GRD. Three positions where alternate splicing inserts short segments in human neurofibromin (T. Nishi, el al., *Oncogene* 6:1555–1559 (1991); D. H. Gutmann et al., *Hum. Mol. Genet.* 2:989–992 (1993); G. Danglot, et al., *Hum. Mol. Gen.* 4:915–920 (1995)) are identified by filled-in triangles. One of these locations corresponds exactly to the position where Drosophila exon 17 is joined to either exon 18a or 18b. Exon 18b includes a translational terminator after a single codon and cDNAs harboring this exon predict a protein ending in PTDKAA (SEQ ID NO: 3). 11 out of 17 Drosophila splice sites map within two codons of splice sites in the human NF1 gene (Y. Li, et al. *Genoinics* 25:9–18 (1995)).

The Drosophila homolog of NF1 is 60% identical to the human NF1 protein over its entire 2802 amino acid length. Although homozygous loss of NF1 is lethal in mice (C. I. Brannan et al., *Genes & Development* 8:1019 (1994)), two viable Drosophila null mutations of NF1 have been generated. There is no NF1 protein detected by protein immunoblotting in these two mutants. $NF1^{P1}$ is a small deletion that includes the NF1 locus and at least two adjacent genes whereas $NF1^{P2}$ represents a P-element insertion. Modulation of voltage-activated K$^+$ currents (Y. Zhong et al., *Neuron* 14:527 (1995); Y. Zhong, *Nature* 375.588 (1995)) induced by the neuropcptide Pituitary Adenylyl Cyclase Activating Polypeptide (PACAP38) is eliminated in these two mutant alleles.

PACAP38 [which belongs to the vasoactive intestinal polypeptide-secretin-glucagon peptide family and stimulates cAMP synthesis through G protein-coupled receptors in vertebrates (A. Arimura, *Regulatory Peptides* 37:287 (1992); D. Spengler et al., *Nature* 365:170 (1993))] induces a 100-fold enhancement of K$^+$ currents by co-activating both Rut-adenylyl cyclase-cAMP and Ras-Raf kinase pathways (Y. Zhong, *Nature* 375:588 (1995)). Mutations in the rut (M. S. Livingstone et al., *Cell* 37:205 (1984)), Ras (M. A. Simon et al., *Cell* 67:701 (1991)), or raf (L. Ambrosio et al., *Nature* 342:288 (1989)) loci eliminate the response to PACAP38 (Y. Zhong, *Nature* 375:588 (1995)). Activation of both cAMP and Ras-Raf pathways together, but not alone, mimics the PACAP38 response (Y. Zhong, 1995)). The involvement of Ras in the PACAP38 response led to the investigation of the effect of NF1 mutations described herein.

The neurofibromatosis type 1 (NF1) tumor suppressor protein partially functions as a Ras-specific guanosine triphosphatase (GTPase) activating protein. Study of Drosophila NF1 mutants reveals that NF1 is essential for the cellular response to the neuropeptide PACAP38 (pituitary adenylyl cyclase-activating polypeptide) at the neuromuscular junction. The peptide induces a 100-fold enhancement of K$^+$ currents by activating the Ras-Raf and adenylyl cyclase-adenosine 3'–5' monophosphate (cAMP) pathways. This response was eliminated in NF1 mutants. NF1 appears to regulate the rutabaga-encoded adenylyl cyclase, rather than the Ras-Raf pathway. Moreover, the NF1 defect was rescued by exposure of cells to pharmacological treatment that increased concentrations of cAMP.

In summary, signaling by the PACAP38 neuropeptide is impaired in NF1 mutants and the defect is apparently caused by a blockade of PACAP38-stimulated activation of Rut-adenylyl cyclase. Thus, the NF1 protein not only acts as a negative regulator of Ras but also as a crucial component for activation of the cAMP pathway. The induced expression of a catalytic subunit of cAMP-dependent protein kinase rescues the developmental phenotype of small body size in $NF1^{P1}$ and $NF1^{P2}$ mutants, providing further support for the above conclusion.

The invention is further illustrated by the following specific examples. These examples should not be construed as limiting the invention in any way.

EXAMPLE 1

Characterization of the Drosophila NF1 Gene.

To analyze NF1 function in an organism amenable to genetic analysis, a conserved Drosophila NF1 homolog was identified. Drosophila NF1 clones were isolated by screening a Canton-S λ, Fix II genomic phage library (Stratagene) in 25'7/0 formamide at 37° C. with a probe representing the C-terminal 1598 amino acids of human NF1. All clones identified represented the same locus. A 13,295 bp segment representing the entire gene was sequenced. A set of 32 overlapping cDNAs was isolated from eye disc, total disc and mixed stage embryo libraries and used to determine 9750 bp of overlapping cDNA sequence. The genomic and cDNA sequences differ in multiple locations, but none of these polymorphisms affect the sequence of the encoded protein. The GenBank accession numbers for the genomic and alternatively spliced CDNA sequences are L26500, L26501 and L26502.

Comparing 13,295 bp of genomic and 9750 bp of cDNA sequence shows that Drosophila NF1 consists of 17 constitutive and 2 alternatively spliced exons 18a and 18b. The alternatively spliced cDNAs predict proteins of 2764 and 2802 amino acids that are 60% identical to the human NF1 protein, neurofibromin (FIGS. 1 and 2). Sequence similarity is observed over the entire length of the proteins, including regions outside of the catalytic GAP-related domain (GRD) or the more extensive segment related to yeast IRA proteins (G. Xu, et al., *Cell* 62:599–608 (1990)). No related sequences were identified during low stringency screens of several cDNA and genomic libraries, indicating that the identified gene is the only Drosophila NF1 homolog. RNA in situ hybridization and staining of embryos and imaginal discs with monoclonal antibodies against the Drosophila protein indicate that NF1 is widely expressed at low levels during all developmental stages. In situ hybridization with single-stranded digoxygenin labeled probes and antibody staining of whole-mount preparations was performed as described (N. H. Patei, in Drosophila melanogaster: *Practical Uses in Cell and Molecular Biology* L. S. B. Goldstein, E. A. Fyrberg, Eds. Academic Press, San Diego, 1994). Monoclonal antibodies against Drosophila NF1 were generated, after immunizing mice with an affinity purified His-tagged fusion protein representing the C-terminal 450 residues of the longer isoform. The Drosophila NF1 gene was mapped to cytogenetic interval 96F and subsequently localized to a 30 kb DNA segment between the bride ofsevenless gene and the Enhancer of split [E(spl)] complex. The NF1 homolog was mapped to cytogenetic interval 96F by in situ hybridization of biotinylated probes to salivary gland chromosomes (W. R. Engels et al., *Focus* 8:6–8; (1996). Using available genomic clones from this region, the gene was subsequently sublocalized to the 30 kb interval between the bride of sevenless and E(spl) loci. This deficiency uncovers the NF1 locus (Hart, A. C. et al., *Genes and Devel.*, 4:1835–1847 (1990)).

To isolate mutant alleles at the NF1 locus, 'local hops' from a strain (K33), which harbors a P-element transposon within the E(spl) complex, approximately 15 kb downstream of NF1, were generated. Inverse PCR was used to screen. Flies were raised on standard medium and crosses carried out at 25° C. To generate NF1 mutants, w;P[w] males homozygous for a P[w] transposon in 96F were crossed to virgin Ki pP Δ2-3 transposase bearing females. Single $F_t$ dysgenic males of genotype w;P[lacZw]/Kip$^P$ Δ2-3 were crossed to w; TM3/TM6B virgin females. Single $F_2$ males of genotype w; P[IacZw]/TM3 or w, P[IacZw]/TM6B were crossed to w;TM3/TM6B virgin females to establish lines with stable novel P-element integrations. The red eyed progeny of this cross was analyzed in pools by inverse PCR (B. Dalby, et al., *Genetics* 139:757–766; (1995). Among 1600 lines screened, two showed evidence of de novo transposon insertions within the NF1 gene. Sequence analysis of cloned insertion sites and detailed mapping showed that in one mutant allele, NF1$^{P1}$, a deletion has removed all of the NF1 gene except for the first exon (FIG. 1A). The deletion extends from the first NF1 intron to the site of the original P-element insertion and as a consequence also removes at least two E(spl) transcripts. The other allele, NF1$^{P2}$, contains a P-element in the first NF1 intron (FIG. 1A). Both alleles fail to express any detectable NF1 protein and hence represent null mutations at this locus.

Unlike NF1-deficient mice (C. I. Brannan, et al. *Genes Dev.* 8:1019–1029 (1994); T. Jacks, et al., *Nature Genetics* 7:353–361 (1994)), Drosophila NF1 mutants are viable and can be maintained as robust homozygous stocks. However, while heterozygotes (NF1/+) show no obvious defects, homozygotes (NF1/NF1) of either allele are 25–30% smaller than the parental K33 strain during all post-embryonic stages. This growth defect is apparent under a variety of culture conditions and mutant animals do not display delayed eclosion or bristle phenotypes that are observed with several Minute mutations (K. Kongsuwan et al., *Nature* 317:555–558 (1985)). The growth defect is fully rescued by expression of an inducible hsNF1 transgene. A hsp70-NF1 mini gene was generated by cloning a hybrid cDNA/ genomic NF1 insert into the SacII and Kpn1 sites of the pKB176PL P-element vector (K. Basler et al., *Science* 243:931–934 (1989)). The genomic segment of the insert harbors three introns and is flanked by MluI and Esp3I sites. This vector was introduced into the germline of w$^{1118}$ flies. Rescue was obtained with daily, 30 minute 37° C. heat shocks.

To determine whether reduced cell proliferation or impaired cell growth underlies the smaller size of NF1 mutants, the wings of wild-type and mutant animals were compared. The linear dimensions of NF1 mutant wings are 25–30% smaller than those of wild-type flies. Since each wing epidermal cell secretes a single hair, cell densities can be determined by counting the number of hairs in a defined region (T. Dobzhansky, *Wilhelm Roux' Archivfuer Entwicklungsmechanik der Organismen* 115:363–379 (1929)). Using this approach, both homozygous NF1 mutants were found to have a 30–40% higher cell density compared to the parental line. Thus, at least in the wings, reduced cell size contributes significantly to the reduction in overall dimensions, implicating NF1 in a process which regulates cell growth. To determine whether the reduced size of wing epidermal cells reflects a cell autonomous defect, X-irradiation was used to induce mitotic recombination in the wings of heterozygous NF1 mutants, using bald and-forked bristle markers to distinguish homozygous mutant clones from surrounding tissue. Clonal analysis was performed in a forked (f) background. Females of genotype f:bld P[f+]TM3 Ser were crossed to either NF1$^{P1}$, NF1$^{P2}$ or K33 males. Parents were removed after 24 hrs and the larval progeny x-irradiated (1000 Rads) after 48–72 hrs. Adult $F_1$ males of genotype f:bld P[f+]/NF1$^{P1}$ or f;bld P[f+]/+ were analyzed. No difference in the distance between wing hairs was observed between multiple NF1$^{-/}$ clones and surrounding tissue. The reduced size of wing cells therefore reflects a non-autonomous requirement for NF1, perhaps reflecting a hormonal deficiency or impaired nutrition or metabolism. However, while smaller cells contribute to the reduced size of wings, the eyes of NF1 mutants show a reduced number of ommatidia of normal size and structure. Furthermore, NF1 deficient embryos are of normal size. Thus, loss of NF1 affects the growth of different tissues in different ways.

EXAMPLE 2

Investigation of the Role of the NF1 Gene Product on Ras Function

Since the only known biochemical property of the NF1 protein is its ability to negatively regulate Ras (T. N. Basu, et al., *Nature* 356:713–715 (1992); J. E. DeClue, et al., *Cell* 69:265–273 (1992); H. A. Kim et al., *Oncogene* 11:325–335 (1995); G. Bollag, et al., *Nat. Genet.* 12:144–148 (1996); D. A. Largaespada et al., *Nat. Genet.* 12:137–143 (1996)), it was surprising that NF1 mutants did not exhibit phenotypic abnormalities associated with excess Ras 1 or Ras 2 activity. Indeed, whereas expression of activated Ras 1 or Ras 2 transgenes results in widespread developmental defects, NF1 mutants are smaller but otherwise patterned normally. The regulation of Ras by NF1 both in vitro and in vivo was therefore examined.

To confirm that Drosophila NF1 can act as a RasGAP, GAP assays with bacterial fusion proteins representing the catalytic domains of human p 120GAP, and human or Drosophila NF1 were performed. GAP assays were performed as described (S. Brill, et al., *Mol. Cell. Biol.* 16:4869–4878 (1996), with appropriately diluted lysates of bacteria expressing soluble fusion proteins. Lysates were standardized for total protein content and fusion protein expression level. The human NF1 and p120-GAP catalytic domain fusion proteins were as described (G. A. Martin, et al., *Cell* 63:843–849 (1990); G. A. Martin et al., *Science* 255:192–194 (1992)). The Drosophila NF1 catalytic domain (amino acids 1235–1614) was cloned into pGEX20. All three fusion proteins stimulated the GTPase activity of H-Ras, but not of the constitutively active H-Ras$^{va112}$ mutant. Thus, Drosophila NF1 clearly functions as a Ras-GAP in vitro.

RAS 1 function in vivo was then examined. The Drosophila Ras 1 protein performs a crucial function in signaling pathways downstream of several receptor tyrosine kinases (RTKs), including Torso and Sevenless. Since minor perturbations in Ras 1 function have phenotypic consequences in each of these pathways, loss of NF1 perturbations of Torso-controlled specification of embryonic terminal structures or Sevenless-mediated photoreceptor differentiation were examined. The pattern of tailless expression, which is regulated by Torso (J. B. Dully et al., *Dev. Biol.* 166:380–95 (1994)), is normal in NF1 deficient embryos. Thus, NF1 does not appear to be an essential regulator of Torso signaling. To test for abnormalities in Sevenless signaling (M. A. Simon et al., *Cell* 67:701–716 (1991); B. Dickson et al., *Curr. Opin. Genet. Dev.* 4:64–70 (1994); L. Bonfini et al., *Science* 255:603–606 (1992)), the retinas of mutant animals were examined. Retinas of NF1$^{P2}$ homozygotes, of NF1'/NF1$^{P1}$ and of NF1$^{P2}$/Df(3R) boss$^{15}$ (17), are completely wild type implying that Ras1-mediated determination of retinal cell fates is unperturbed. This deficiency uncovers the NF1 locus (A. C. Hart et al., *Genes and Devel.* 4:1835–1847 (1990). In homozygotes of NF1$^{P1}$, 25% of ommatidia have one or more extra photoreceptor cells (not shown). However, this phenotype may be due to deletion of genes within the neurogenic E(spl) complex, which has occurred in the NF1$^{P1}$ allele. A particularly sensitive indicator of Sevenless pathway function is the sevr$^{E4}$; Sos$^{JC2}$/+ mutant combination. Only approximately 17% of ommatidia in this double mutant have R7 cells, and this number is very sensitive to alterations in the gene dosage of Ras1 pathway components (R. D. Rogge et al., *Cell* 64:39–48 (1991)). Flies of this genotype which are also heterozygous for NF1$^{P2}$ had no significant alteration in the fraction of R7 containing ommatidia (not shown). Thus, at least two Ras1-mediated signaling pathways downstream of RTKs were not influenced by a reduction in NF1 function.

Although NF1 does not appear to be a major regulator of Ras1 in RTK-mediated signaling, the NF1 deficient phenotype may still reflect improper regulation of other less well characterized functions of Ras1, e.g., in signaling downstream of G-protein-coupled receptors. If so, then manipulating the level or activity of Ras1 pathway components may modify the NF1 deficient phenotype. Loss of function mutants used in this work include: Sos$^{e2H}$, Ras1$^{e1B}$, Ras1$^{e2F}$ (M. A. Simon et al., *Cell* 67:701–716 (1991)), and DCO$^{3B}$, Df(2L)Tw2 (D. Kalderon et al., *Genes Dev.* 2:1539–56 (1988); M. E. Lane et al., *Genes Dev.* 7:1229–43 (1993)). Raf$^{gof}$ is an activated allele of Drosophila Raf (A. H. Brand et al., *Genes Dev.* 8:629–639 (1994)). hsp70-PKA* flies harbor a murine PKA transgene with His87Gln and Trp196Arg substitutions that block interaction with the PKA regulatory subunit (J. Jiang et al., *Cell* 80:563–572 (1995)). Expression of this gene was induced by daily, 30 minute 37° C. heat shocks or by growing cultures at 25° C. However, heterozygous loss of Ras1 or Sos had no effect on the size of NF1 mutant pupae, nor did crossing in an activated Raf$^{gof}$ mutation. Neither reducing nor increasing signaling through the Ras1 -Raf pathway therefore modifies the NF1 phenotype. This raised the possibility that the NF1 mutant phenotype may not involve Ras-Raf mediated signaling.

EXAMPLE 3

Role of the NF1 Gene Product in the Adenylyl Cyclase-Protein Kinase Pathway.

Other workers previously observed that flies carrying a viable heteroallelic combination of mutant alleles of the gene encoding the PKA catalytic subunit, DCO, were reduced in size (E. M. Skoulakis et al., *Neuron* 11:197–208 (1993)). For this reason and because an electrophysiological phenotype of NF1 mutants is rescued by cAMP, the cAMP-PKA pathway representing an alternate target for NF1 was tested. Pupae from a heteroallelic combination of DCO mutations (DCO$^{TW2}$/DCO$^{B3}$) were examined and it was found that these are phenotypically indistinguishable from NF1 mutants. Whether increasing PKA activity in NF1 mutant animals would rescue the size defect was then tested. This was achieved by expressing a constitutively active murine PKA catalytic subunit transgene in an NF1 mutant background. Heat shock induced expression of this mutant protein, resulted in lethality. However, lower levels of transgene expression were achieved by growing the cultures at 25° C. Under these conditions, significant rescue of the pupal size defect was consistently observed. In contrast to its effect on NF1 mutant pupae, the PKA transgene did not modify the phenotype of Tubby, a mutation that results in pupae of small size. The dominant Tubby (Tb) mutation maps to 3–90.6, near NF1 (D. L. Lindsley et al., *The Genetics and Biology of Drosophila melanogaster*, Academic Press, San Diego, 1992). However, 2.9% genetic recombination observed between Tb and the P[w] transposon in the K33 strain indicates that Tb is not an allele of NF1. Nor were wild-type flies expressing the PKA transgene observed to be larger. Since expression of activated PKA suppresses the phenotype of null alleles of NF1, PKA cannot function upstream of NF1 in a simple linear pathway. Therefore, PKA must either function downstream of NF1 or in a parallel pathway.

In addition to their reduced size, NF1 mutants also display a behavioral defect characterized by a diminished escape response. Thus, in an assay that determines the number of flies that escape either spontaneously within 90 seconds of release or after repeated prodding (S. Richards et al., *Genetics* 142:1215–1223 (1996)), approximately 15% of either NF1 mutant (n=200) failed to respond, as compared to 3% non-responders for the parental K33 strain. The reduced escape rate does not reflect obvious anatomical defects of the peripheral nervous system or the musculature, and the mutants scored within normal limits in tests measuring their activity or their response to visual or olfactory stimuli (R. Wehner, *J Insect Physiol.* 18:1531–1543 (1972); P. Monte, et al., *Behavior Genetics* 19:267–283 (1989)). Because opening of a post-synaptic K$^+$ channel in the larval neuromuscular junction requires both Ras1 and adenylyl cyclase (Y. Zhong, *Nature* 375:588–592 (1995)), it seemed possible that aberrant neuromuscular function might explain the diminished escape response. Indeed as described further below, a specific electrophysiological defect was demonstrated at the larval neuromuscular junction, which is rescued by pharmacological manipulation of the cAMP-PKA pathway and is insensitive to manipulation of Ras1-mediated signaling. Therefore, activation of PKA rescues at least two phenotypes associated with loss of NF1.

EXAMPLE 4

Requirement of Drosophila NF1 Protein for Activation of Adenylyl Cyclase by PACAP38-like Neuropeptides PACAP38-induced responses were recorded by the two-microelectrode voltage-clamp method from body-wall muscle fibers of larvae at the third instar (Y. Zhong, *Nature* 375:588 (1995); A. Arimura, *Regulatory Peptides* 37:287 (1992); D. Spengler et al., *Nature* 365:170 (1993); L. Y. Jan et al., *J. Physiol.* 262:189 (1976); C.-F. Wu et al., *Science* 220:1076 (1983); B. A. Stewart et al., *J Comp. Physiol.* 175:179 (1994)). Electrophysiological recording: The larval body-wall neuromuscular preparation has been described (Y. Zhong et al., *Neuron* 14:527 (1995); Y. Zhong, *Nature* 375:588 (1995); L. Y. Jan et al., *J Physiol.* 262:189 (1976); C.-F. Wu et al., Science 220:1076 (1983); B. A. Stewart et al., *J Comp Physiol.* 175:179 (1994)). The setup, saline, recording conditions and voltage paradigms were as described (Y. Zhong et al., *Neuron* 14:527 (1995); Y. Zhong, *Nature* 375:588 (1995)). For recording the PACAP38-induced synaptic current, the membrane potential was clamped at −80 mV. For recording $K^+$ currents, command voltages were stepped from the holding potential of −80 to −50 and +20 mV, respectively. These currents include outward $K^+$ and inward $Ca^{2+}$ currents, but the inward $Ca^{2+}$ component is completely masked (S. Singh et al., *Neuron* 2:1325 (1989)). PACAP38 was applied by pressure ejection through a glass electrode positioned near the voltage-clamped muscle membrane. Forskolin and cAMP analogs were applied to the solution bathing the preparation. Perfusion of PACAP38 to the neuromuscular junction induced an inward current followed by a 100-fold enhancement of $K^+$ currents in wild-type larvae (Y. Zhong et al., *Neuron* 14:527 (1995); Y. Zhong, *Nature* 375:588 (1995)). In $NF1^{P1}$ and $NF1^{P2}$ mutants, the inward current remained mostly intact, but the enhancement of $K^+$ currents was abolished. Because the inward current is not affected in NF1 mutants, it appears that PACAP38 receptors are normally activated by the peptide in these mutants.

To rule out potential developmental effects of the NF1 mutation, transgenic flies carrying an inducible normal NF1 gene were studied. The hsNF1 transgene was expressed after heat shock in transgenic NF1 mutants, hsNF1; $NF1^{P1}$ and hsNF1; $NF1^{P2}$. PACAP38-induced enhancement of $K^+$ currents was observed in hsNF1; $NF1^{P1}$ larvae subjected to heat shock (37° C. for 1 hour) and not in those without heat shock. hsNF1; $NF1^{P2}$ larvae, however, showed a normal response to PACAP38 even in larvae not subjected to heat shock. This was probably the result of constitutive expression of the hsNF1 transgene because a large amount of NF1 protein was detected in these flies. To reduce the amount of hsNF1 expression, hsNF1; $NF1^{P2}/+$; $NF1^{P2}$ larvae were selected in which only one copy of the hsNF1 transgene was present. In these larvae, the PACAP38 response was only observed after heat shock. The PACAP38-induced enhancement was fully rescued 4 hours after heat shock, but was observed with a smaller enhancement as early as 1.5 hours after heat shock. Such a time course suggests that all other components in the PACAP38 signaling pathways remain intact so that the preparation resumes PACAP38 responsiveness as soon as enough NF1 protein is synthesized.

Because PACAP38 is a vertebrate peptide (A. Arimura, *Regulatory Peptides* 37:287 (1992); D. Spengler et al., *Nature* 365:170 (1993)), the response induced by endogenous PACAP38-like neuropeptide was tested (Y. Zhong et al., *Neuron* 14:527 (1995); Y. Zhong, *Nature* 375:588 (1995)). High frequency stimulation (40 Hz) applied to motor axons through a suction pipette increased $K^+$ currents, presumably by causing release of PACAP38-like peptides (Y. Zhong et al., *Neuron* 14:527 (1995)). This evoked PACAP3 8-like response was also eliminated in NF1 mutants and rescued by the expression of the hsNF1 transgene.

Because the NF1 protein acts as a Ras-GAP (G. F. Xu, et al., *Cell* 62:599 (1990); *Cell* 63:835 (1990); A. M. Buchberg et al., *Nature* 347:291 (1990); R. Ballester et al., *Cell* 63:851 (1990); G. A. Martin et al., *Cell* 63:843 (1990)), two null alleles of Drosophila Gap1, $rI^{533B1}$ and $rI^{533PB}$ were examined. Flies carrying the mutations have disrupted eye development that results from increased Ras activity (U. Gaul et al., *Cell* 68:1007 (1992)). PACAP38 induced a normal enhancement of $K^+$ currents in both Gap1 mutants. Moreover, recordings from transgenic larvae showed that induced expression of constitutively active Ras ($Ras^{V12}$) (M. E. Fortini et al., *Nature* 355:559 (1992)) or active Raf protein kinase ($Raf^{gof}$) (A. H. Brand et al., *Genes & Development* 8:629 (1994)) neither blocked nor mimicked the PACAP38 response (Y. Zhong, *Nature* 375:588 (1995)). These results suggest that failure to negatively regulate Ras-Raf signaling does not explain the defective PACAP38 response in NF1 mutants.

Application of the membrane permeable cAMP analogs, dibutyryl cAMP or 8-bromo cAMP to the larval neuromuscular preparation is insufficient to produce the PACAP38-like enhancement of $K^+$ currents (Y. Zhong, *Nature* 375:588 (1995); Y. Zhong et al., *J. Neurogenet.* 9:15 (1993)) and appeared not to disrupt the PACAP38 response in wild-type larvae. This implies that cAMP may not cause inhibition of the Raf activity as reported in other preparations (S. J. Cook et al., *Science* 262:1069 (1993)). Application of these cAMP analogs to NF1 mutants did restore the normal response to PACAP38. Both $NF1^{P2}$ homozygotes and heteroallelic $NF1^{P1}/NF1^{P2}$ larvae showed enhanced $K^+$ currents. $NF1^{P1}$ larvae also responded, but with a smaller amplitude of response, which may be a non-specific effect of genetic background because the response of $NF1^{P1}/NF1^{P2}$ heterozygotes to PACAP38 was fully restored by treatment with cAMP analogs.

The cAMP analogs were effective if applied any time before or within 2 min. after applying PACAP38. After 2 min, cAMP analogs failed to enhance the response of $NF1^{P2}$ mutants to PACAP38. This time course is consistent with a model whereby in NF1 mutants, the Ras-Raf pathway is normally activated in response to PACAP38 for 2 min, but the cAMP pathway is blocked. Therefore, synergistic modulation of $K^+$ currents can be achieved if cAMP analogs are supplied during the transient activation of the Ras-Raf pathway. Addition of cAMP analogs also restored the response to PACAP38 in $rut^1$ mutants, but not in $Ras^{12a}$ mutants (M. S. Livingstone et al., *Cell* 37:205 (1984); L. R. Levin et al., *Cell* 68:479 (1992); Y. Zhong, *Nature* 375:588 (1995)).

To further test whether activation of cAMP signaling rescues the defective PACAP response of NF1 mutants, the drug forskolin, which stimulates G-protein coupled adenylyl cyclase activity (K. B. Seamon et al., *J Cyclic Nucleotide Res.* 22:201 (1981); Y. Dudai et al., *J Neurogenet.* 2:365 (1985)), was applied to the neuromuscular preparation. PACAP38 induced a normal response in $NF1^{P2}$ and $NF1^{P1}/NF1^{P2}$ mutants exposed to forskolin. This indicates that adenylyl cyclase is present, but is not activated by receptors for PACAP38-like neuropeptides. Forskolin also restored the PACAP38 response in $rut^1$ mutants even though the Rut-adenylyl cyclase is completely nonfunctional (M. S. Livingstone et al., *Cell* 37:205 (1984); L. R. Levin et al., *Cell* 68:479 (1992)). It is possible that cAMP synthesized by other adenylyl cyclases upon forskolin stimulation is sufficient to modulate $K^+$ currents together with the Ras pathway activated by PACAP38 (M. S. Livingstone, *Proc Natl Acad Sci USA* 82:5992 (1985)).

Adenylyl cyclase shows abnormal subcellular localization in yeast IRA mutants (M. R. Mitts et al., *Mol Cell Biol* 11:591, (1991)). The IRA gene encodes proteins that are distantly related to the NF1 protein and that are involved in mediating Ras-dependent activation of adenylyl cyclase. Although the yeast cyclase is very different from Rut-adenylyl cyclase and other cyclases in higher organisms (T. Toda et al., *Cell* 40:27 (1985); K. Tanaka et al, *Cell* 60:803 (1990)), adenylyl cyclase activity in membrane fractions was examined. Adenylyl cyclase activity was assayed as described (M. S. Livingstone et al., *Cell* 37:205 (1984)) with membranes from abdomens of rut[1], NF1[P2], and wild type flies. Calcium concentrations were calculated according to MaxChelator v1.31 (D. M. Bers et al., *Methods Cell. Biol.* 40:3 (1994)). Assays were done in duplicate and each result represents data from at least two separate experiments. The Rut-adenylyl cyclase is the only cyclase that can be activated by $Ca^{2+}$-calmodulin (CaM) in the tissues from fly abdomen, as indicated by the lack of the $Ca^{2+}$-dependent cyclase activity in rut[1] mutants (M. S. Livingstone et al., *Cell* 37:205 (1984); L. R. Levin et al., *Cell* 68:479 (1992)). In addition, the basal activity (M. S. Livingstone et al., *Cell* 37:205 (1984)) and the forskolin-stimulated (Y. Dudai et al., *J Neurogenet.* 2:365 (1985)) activity of adenylyl cyclase were also reduced in rut[1] mutants. However, NF1 mutations did not affect the basal activity, the $Ca^{2+}$-dependent activity, or the forskolin-stimulated activity of adenylyl cyclase. Therefore, Rut-adenylyl cyclase is present in these membranes and can be normally activated by $Ca^{2+}$-CaM and forskolin.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method of determining the ability of a compound to stimulate cyclic AMP formation comprising:
   (a) obtaining a cellular sample that has a defect in the amount or activity of NF1 protein;
   (b) applying said compound to an aliquot of said cellular sample;
   (c) determining the amount of cyclic AMP produced by said aliquot;
   (d) adding NF1 protein to another aliquot of said cellular sample;
   (e) applying said compound to said another aliquot of said cellular sample; and
   (f) determining the amount of cyclic AMP produced by said another aliquot;

wherein an increase in the production of cyclic AMP in step (f) compared with that in step (c) demonstrates the ability of said compound to stimulate cyclic AMP formation.

2. The method of claim 1 wherein the determination of the amount of cyclic AMP is accomplished by measuring the activity of protein kinase A.

3. The method of claim 1 wherein said cyclic AMP is synthesized by rut-adenylyl cyclase.

* * * * *

UNITED STATES PATENT AND TRADEMARK OFFICE
CERTIFICATE OF CORRECTION

PATENT NO. : 6,261,761 B1
DATED : July 17, 2001
INVENTOR(S) : Yi Zhong and Hiu-Fu Guo It is certified that error appears in the above-identified patent and that said Letters Patent is hereby corrected as shown below:

Column 1,
Line 12, just before "Background of the Invention", insert:
-- GOVERNMENT SUPPORT This invention was made with Government support, in whole or in part, under Grant No. NIH R01-NS34779 awarded by the National Institutes of Health. The United States government has certain rights in this invention. --

Signed and Sealed this

Seventh Day of September, 2004

JON W. DUDAS
*Director of the United States Patent and Trademark Office*